(12) United States Patent
Kawamura et al.

(10) Patent No.: US 8,389,000 B2
(45) Date of Patent: Mar. 5, 2013

(54) ADHESIVE SKIN PATCH AND METHOD FOR EVALUATION OF ADHESIVE SKIN PATCH

(75) Inventors: Naohisa Kawamura, Kasukabe (JP); Takashi Saitoh, Kasukabe (JP); Junko Tsuchiya, Kasukabe (JP)

(73) Assignee: Nipro Patch Co., Ltd., Saitama (JP)

( * ) Notice: Subject to any disclaimer, the term of this patent is extended or adjusted under 35 U.S.C. 154(b) by 367 days.

(21) Appl. No.: 12/312,877

(22) PCT Filed: Nov. 29, 2007

(86) PCT No.: PCT/JP2007/073055
§ 371 (c)(1),
(2), (4) Date: May 28, 2009

(87) PCT Pub. No.: WO2008/066115
PCT Pub. Date: Jun. 5, 2008

(65) Prior Publication Data
US 2010/0028411 A1    Feb. 4, 2010

(30) Foreign Application Priority Data
Nov. 30, 2006 (JP) .................................. 2006-324460

(51) Int. Cl.
*A61L 15/16* (2006.01)
*A61F 13/02* (2006.01)
*A61F 13/00* (2006.01)
*A61K 9/70* (2006.01)

(52) U.S. Cl. ................... 424/448; 424/447; 424/449

(58) Field of Classification Search .............. 424/447, 424/448, 449
See application file for complete search history.

(56) References Cited

U.S. PATENT DOCUMENTS
4,460,364 A   7/1984   Chen et al.

FOREIGN PATENT DOCUMENTS

| | | |
|---|---|---|
| EP | 1072261 | 1/2001 |
| EP | 1072261 A2 * | 1/2001 |
| JP | 59/058068 | 4/1984 |
| JP | 60-004125 | 1/1985 |
| JP | 63-246327 | 10/1988 |
| JP | 04-321624 | 11/1992 |
| JP | 07-165563 | 6/1995 |
| JP | 10-507944 | 8/1998 |
| JP | 2001-039864 | 2/2001 |
| JP | 2001-507591 | 6/2001 |
| JP | 2001-507962 | 6/2001 |
| JP | 2001-508053 | 6/2001 |
| JP | 2001-508094 | 6/2001 |
| JP | 2001-302502 | 10/2001 |
| JP | 2001-328935 | 11/2001 |
| JP | 2002-226366 | 8/2002 |
| JP | 2002-363070 | 12/2002 |
| JP | 2003-183156 | 7/2003 |
| JP | 2004-083462 | 3/2004 |
| JP | 2004-315542 | 11/2004 |
| JP | 2006-169160 | 6/2006 |
| JP | 2007-008927 | 1/2007 |
| WO | 96/13238 | 5/1996 |
| WO | 98/28018 | 7/1998 |
| WO | 98/28020 | 7/1998 |
| WO | 98/28021 | 7/1998 |
| WO | 98/28022 | 7/1998 |
| WO | 01/43279 | 6/2001 |
| WO | 01/68061 | 9/2001 |
| WO | 2005/087282 | 9/2005 |
| WO | 2006-129745 | 12/2006 |

\* cited by examiner

*Primary Examiner* — Fereydoun G Sajjadi
*Assistant Examiner* — Michael B Pallay
(74) *Attorney, Agent, or Firm* — Dilworth & Barrese, LLP (57) ABSTRACT

Disclosed is an adhesive skin patch having an SIS block copolymer as an adhesive component, which has an improved handling property and can reduce irritation to a user. The adhesive skin patch comprises a flexible substrate and an adhesive layer laminated on the substrate, wherein the adhesive layer comprises a styrene-isoprene-styrene block copolymer. In the adhesive skin patch, the tan δ value of the adhesive agent as determined by measuring a dynamic viscoelasticity at 32° C. satisfies a requirement represented by the following formula 1 at at least one frequency laying between 0.04 to 0.25 Hz. $0.25x+0.05 \leqq y \leqq 0.25x+0.10$ (formula 1) [wherein x represents a frequency (Hz); and y represents a tan δ value.]

8 Claims, 3 Drawing Sheets

ADHESIVE SKIN PATCH AND METHOD FOR EVALUATION OF ADHESIVE SKIN PATCH

TECHNICAL FIELD

The present invention relates to a skin patch, and more particularly, relates to a skin patch having an adhesive layer including a styrene-isoprene-styrene block copolymer. In addition, the present invention relates to a method for evaluating characteristics of a skin patch.

BACKGROUND ART

Conventionally, skin patches (for example, plasters) for applying on skin have been extensively used. The adhesion (pressure-sensitive adhesion) of the skin patches to the skin is important because it allows drugs to be transdermally absorbed through application to the skin.

Thus, the adhesion of skin patches has been extensively studied. Attempts to use a styrene-isoprene-styrene block copolymer (hereinafter, may be also referred to as "SIS block copolymer") as an adhesive component has been made in light of the possibility of production by heat fusion without using a solvent.

For example, a skin patch including indometacin, an SIS block copolymer, liquid paraffin and polyethylene glycol in the adhesive layer (see, Patent Document 1), a skin patch including an SIS block copolymer, crotamiton, and an anti-inflammatory analgesic drug (see, Patent Document 2), and the like have been disclosed.

These skin patches can be produced by heat fusion without using a solvent because an SIS block copolymer was included in the adhesive layer, thus enabling easy and inexpensive production, and a reduced environmental burden can be realized.

Patent Document 1: Japanese Unexamined Patent Application, Publication No. 2001-302502
Patent Document 2: Japanese Unexamined Patent Application, Publication No. H4-321624

DISCLOSURE OF THE INVENTION

Problems to be Solved by the Invention

However, conventional skin patches as described above are accompanied by the following problems. First, since the aforementioned skin patches have excessively strong self-adhesion (herein, "self-adhesion" is defined as cohesive force, attachment properties and the like between adhesive layer faces of a skin patch, without excluding adhesion to objects other than the adhesive layer face), the adhesive layer faces are likely to be attached with each other when the release film is peeled, when the skin patch is applied to the skin, or when the patch is applied once again, and thus peeling of the attached faces may be difficult.

Second, because the aforementioned skin patches have excessively strong adhesion also to skin, significant pain may be experienced by a user when peeling a skin patch from the skin.

Accordingly, an object of the present invention is to provide a skin patch in which an SIS block copolymer is used as an adhesive component, and which can improve the handleability, and can reduce the amount of irritation that a user experiences.

Means for Solving the Problems

The present inventors found that handleability can be improved, and irritation that a user experiences can be reduced by defining tan $\delta$ of the adhesive as determined by measurement of the dynamic viscoelasticity at 32° C. to fall within a predetermined range. Accordingly, the present invention was accomplished. More specifically, the present invention provides the following aspects.

According to a first aspect of the invention, a skin patch including a flexible backing, and an adhesive layer laminated on the backing is provided, the adhesive layer includes a styrene-isoprene-styrene block copolymer, and has a tan $\delta$ value, which was determined by measurement of dynamic viscoelasticity at 32° C., that satisfies the following formula 1 on at least one point in a range of frequency of 0.04 Hz to 0.25 Hz.

$$0.25x+0.05 \leq y \leq 0.25x+0.10 \qquad \text{Formula 1}$$

(wherein, x represents a frequency (Hz), and y represents tan $\delta$.)

In a second aspect of the skin patch according to the first aspect of the present invention, the tan $\delta$ value determined by measurement of dynamic viscoelasticity at 32° C. satisfies the above formula 1 on an arbitrary point in a range of frequency of 0.04 Hz to 0.25 Hz.

According to a third aspect of the invention, a skin patch including a flexible backing, and an adhesive layer laminated on the backing, the adhesive layer includes a styrene-isoprene-styrene block copolymer, and has a tan $\delta$ value, which was determined by measurement of dynamic viscoelasticity at 32° C., that satisfies the following formula 2 on at least one point in a range of frequency of 0.04 Hz to 0.10 Hz.

$$0.25x+0.05 \leq y \leq 0.65x+0.09 \qquad \text{Formula 2}$$

(wherein, x represents a frequency (Hz), and y represents tan $\delta$.)

In a fourth aspect of the skin patch according to the third aspect of the present invention, the tan $\delta$ value determined by measurement of dynamic viscoelasticity at 32° C. satisfies the above formula 2 on an arbitrary point in a range of frequency of 0.04 Hz to 0.10 Hz.

In a fifth aspect of the skin patch according to any one of the first to the fourth aspects of the present invention, the adhesive layer further includes a tackifier, and a plasticizer.

In a sixth aspect of the skin patch according to the fifth aspect of the present invention, the content of the styrene-isoprene-styrene block copolymer is no less than 10% by mass and no greater than 40% by mass; the content of the tackifier is no less than 10% by mass and no greater than 35% by mass; and the content of the plasticizer is no less than 20% by mass and no greater than 60% by mass based on the mass of the entire adhesive layer.

In a seventh aspect of the skin patch according to any one of the first to the sixth aspects of the present invention, the styrene-isoprene-styrene block copolymer has a mass ratio of styrene to isoprene (styrene/isoprene) of no less than 20/80 and no greater than 25/75.

According to an eighth aspect of the invention, a method for performing evaluation of a skin patch including a flexible backing, and an adhesive layer laminated on the backing, the evaluation is performed based on a tan $\delta$ value determined by measurement of dynamic viscoelasticity of the adhesive layer at a temperature of a subject to which the skin patch is applied.

Effects of the Invention

According to the present invention, since the tan $\delta$ value determined by measurement of dynamic viscoelasticity at 32°

C. in the region of the frequency being no less than 0.04 Hz and no greater than 0.25 Hz is defined to fall within a predetermined range, handleability can be improved, and the irritation that a user experiences can be reduced with respect to a skin patch in which an SIS block copolymer is used as an adhesive component.

In addition, according to the present invention, since the tan δ value determined by measurement of dynamic viscoelasticity at 32° C. in the region of the frequency being no less than 0.04 Hz and no greater than 0.10 Hz is defined to fall within a predetermined range, handleability can be improved, and the irritation that a user experiences can be reduced with respect to a skin patch in which an SIS block copolymer is used as an adhesive component.

PREFERRED MODE FOR CARRYING OUT THE INVENTION

Hereinafter, a first example of an embodiment of the present invention will be explained; however, the present invention is not limited to the following embodiment.

The skin patch of the present invention includes a flexible backing, and an adhesive layer laminated on the backing. Herein, the skin patch of the present invention is principally for application to skin, and may include plasters, cataplasms, tapes, adhesive plasters, sheets, wound dressings, cosmetic facial masks and the like, however, industrial tapes are not included.

Adhesive Layer

The adhesive layer that constitutes the skin patch includes an SIS block copolymer as an essential component, and preferably, further includes a tackifier and a plasticizer. Herein, the entirety of the components included in the adhesive layer is referred to as "adhesive".

SIS Block Copolymer

The SIS block copolymer is a type of rubber-based adhesive, and belongs to an A-B-A type polymer, which is a styrene thermoplastic elastomer having a molecular structure in which "A" as end blocks represents polystyrene, and "B" as intermediate block represents polyisoprene.

The SIS block copolymer which may be used in the present invention is not particularly limited, but in general, may have a solution viscosity (MPa s [cps], 25° C.) of about 100 to 3000, and have a mass ratio of styrene to isoprene of 10/90 to 30/70. Preferably, the mass ratio of styrene to isoprene (styrene/isoprene) is 20/80 to 25/75. By using such an SIS block copolymer having a high mass ratio of styrene, preparation of the adhesive is facilitated.

Specifically, the following commercial SIS based resins can be used. For example, one having a styrene/rubber ratio (% by mass) of 15/85 and a solution viscosity (MPa s [cps], 25° C.) of 1,500 (trade name: Kraton D-1107), one having a styrene/rubber ratio (% by mass) of 15/85 and a solution viscosity (MPa s [cps], 25° C.) of 900 (trade name: Kraton D-1112), one having a styrene/rubber ratio (% by mass) of 17/83 and a solution viscosity (MPa s [cps], 25° C.) of 500 (trade name: Kraton D-1117P), one having a styrene/rubber ratio (% by mass) of 22/78 (trade name: Kraton D-KX401), one having a styrene/rubber ratio (% by mass) of 16/84 (trade name: Kraton D-KX406), one having a styrene/rubber ratio (% by mass) of 30/70 and a solution viscosity (MPa s [cps], 25° C.) of 300 (trade name: Kraton D-1125x), one having a styrene/rubber ratio (% by mass) of 10/90 and a solution viscosity (MPa s [cps], 25° C.) of 2,500 (trade name: Kraton D-1320x) are included (all manufactured by Kraton JSR Elastomers K.K.). The SIS block copolymer used in the present invention may include one, or two or more of these products, and one having a styrene/rubber ratio (% by mass) of 22/78 (trade name: Kraton D-KX401) is preferred.

The content of the SIS block copolymer is not particularly limited, and it is preferably 10 to 40% by mass based on the mass of the entire adhesive. An exceedingly low content of the SIS block copolymer is not preferred because the cohesion becomes insufficient. In contrast, an exceedingly high content is also not preferred because adhesion to the skin becomes insufficient.

Tackifier

The tackifier which may be used in the present invention is not particularly limited, and for example, alicyclic saturated hydrocarbon resins (synthetic petroleum resin) as well as rosin ester derivatives, terpene based resins, phenolic resins and the like are preferred.

The alicyclic saturated hydrocarbon resin is not particularly limited, and for example, "ARKON P-100 (trade name)" (manufactured by Arakawa Chemical Industries, Ltd.) and the like may be exemplified.

The rosin ester derivative is not particularly limited, and for example, "Ester Gum H (trade name)" (manufactured by Arakawa Chemical Industries, Ltd.), "KE-311 (trade name)" (manufactured by Arakawa Chemical Industries, Ltd.), "KE-100 (trade name)" (manufactured by Arakawa Chemical Industries, Ltd.), and the like may be exemplified.

The terpene based resin is not particularly limited, and for example, "YS resin (trade name)" (manufactured by YASUHARA CHEMICAL Co., Ltd.) and the like may be exemplified.

The tackifier used in the present invention may include, for example, any one, or two or more of these agents.

The content of the tackifier is not particularly limited, and is preferably 10 to 35% by mass based on the mass of the entire adhesive. When the content of the tackifier is too low, the adhesion becomes insufficient. In contrast, when the content of the tackifier is too high, the adhesion becomes excessively great, thus a user may experience significant pain when a skin patch is peeled from the skin.

Plasticizer

The plasticizer which may be optionally employed in the present invention is not particularly limited and, for example, liquid paraffins, hydrogenated oils, hydrogenated castor oil, higher alcohols such as octyldodecanol, squalane, squalene, castor oil, liquid rubbers (polybutene), fatty acid esters such as isopropyl myristate, and the like may be exemplified. The plasticizer used in the present invention may include, for example, any one, two or more of these compounds. Moreover, among these, liquid paraffins, hydrogenated oils, and hydrogenated castor oils are preferred.

The content of the plasticizer is preferably 20 to 60% by mass based on the mass of the entire adhesive. When the content of the plasticizer is too low, the adhesion becomes insufficient because the adhesive layer is excessively hardened. In contrast, when the content of the plasticizer is too high, the adhesive layer is excessively softened, whereby stickiness may result, and thus a user may experience significant pain when peeling a skin patch from the skin, or residual adhesive is likely to remain. The content of the plasticizer is more preferably 25 to 50% by mass, and still more preferably 30 to 50% by mass.

Optional Ingredient

The adhesive layer that constitutes the skin patch may contain, as needed, any optional ingredients such as medicinal ingredients, excipients, anti-oxidizing agents, drug solubilizers, transdermal absorption promoting agents, flavors, colorants and the like, in addition to the ingredients described above. The optional ingredient may include any one, two or more of these.

Medicinal Ingredient

As the medicinal ingredient, for example, general anesthetics, sleeping drugs, analgesics, antiphlogistic analgetics, steroid hormonal drugs, analeptic stimulant drugs, drugs for psychoneurosis, topical anesthetics, skeletal muscle relaxants, drugs for autonomic nerve, anti-allergic drugs, antihistamic drugs, cardiac stimulants, drugs for arrhythmia, diuretic drugs, hypotensive drugs, vasoconstrictors, vasodilators, calcium antagonists, anti-bacteriocides, drugs for parasitism-developed skin diseases, skin softening agents, antibiotics, antidotes, antitussive drugs, antipruritic drugs, hypnotics, spiritual exaltation agents, antiasthmatics, hormone secretion accelerators, antiulcer drugs, antitumor drugs, vitamins, agents having a whitening effect such as ingredients for beautiful skin, and the like may be included.

Moreover, when the intended use of the skin patch of the present invention is for a topically acting skin patch, the following drugs may be included therein, for example, an antiphlogistic analgetic such as indometacin, ketoprofen, flurbiprofen, loxoprofen, loxoprofen sodium, piroxicam, meloxicam, ketorolac, felbinac, diclofenac, diclofenac sodium, or the like. Among these, at least one selected from the group consisting of indometacin, ketoprofen, felbinac, loxoprofen, diclofenac, and salts thereof is preferable. The content of the drug is not particularly limited, and may be generally approximately 0.1 to 20% by mass based on the mass of the entire adhesive layer.

Excipient

The excipient is not particularly limited, and examples thereof include silicon compounds such as silicate anhydride, light silicate anhydride and hydrous silicic acid, cellulose derivatives such as ethyl cellulose, methyl cellulose, hydroxypropyl cellulose and hydroxypropylmethyl cellulose, water soluble polymers such as polyvinylalcohol, aluminum compounds such as dry aluminum hydroxide gel and hydrous aluminum silicate, kaolin, titanium oxide, and the like.

Anti-Oxidizing Agent

The anti-oxidizing agent is not particularly limited, and for example, dibutylhydroxytoluene, ascorbic acid, tocopherol, tocopherol ester derivatives, butylhydroxyanisole, 2-mercaptobenzimidazole, and the like may be exemplified.

Solubilizer and Transdermal Absorption Promoting Agent of Drug

The solubilizer, and the transdermal absorption promoting agent of the drug are not particularly limited, and polyhydric alcohols such as polyethylene glycol (average molecular weight: 200 to 30000), glycerin, ethylene glycol and diethylene glycol, fatty acids such as oleic acid, isostearic acid and citric acid, fatty acid esters such as isopropyl myristate, isopropyl palmitate and diisopropyl adipate, fatty acid polyhydric alcohol esters such as caprylic acid monoglyceride, caprylic acid triglyceride and sorbitan fatty acid esters, terpenes such as menthol, menthol derivatives, peppermint oil and limonene, N-methyl-2-pyrrolidone, crotamiton, polyvinylalcohol, and the like are exemplified.

Backing

The backing used in the present invention is not particularly limited, and stretch or nonstretch woven fabrics, or nonwoven fabrics of polyethylene, polypropylene or the like, films of polyethylene, polypropylene, an ethylene acetate vinyl copolymer, vinyl chloride or the like, or foam backings of urethane, polyurethane or the like can be used. The backing may include any one of these alone, or two or more of these may be used as a laminate.

Liner

The skin patch of the present invention has a flexible backing and an adhesive layer provided by applying an adhesive on one face of the backing, and is generally provided in a form in which a releasable liner is laminated additionally on the adhesive layer.

As the releasable liner, which is typically used in the present invention, a film of polyethylene, polypropylene, an ethylene vinyl acetate copolymer, vinyl chloride or the like, a metal film prepared by aluminum vapor deposition or the like may be exemplified, and the liner surface subjected to a release treatment such as a silicon treatment or the like may be included. As the "releasable liner" used in the present invention, for example, those having a linear or curved cut, those in which two or more liners overlap in part, and those having a turned edge may be preferably employed in view of easy release thereof.

Method of Manufacture

Production of Adhesive

For the skin patch of the present invention, an adhesive is prepared by mixing a raw material composition which includes an SIS block copolymer, while stirring in a Henschel mixer (registered trade name) or the like under a shear loading condition (stirring speed: 50 rpm to 1500 rpm) from initiation of fusion until a fused state is reached (from room temperature to 250° C.), and additionally mixing of the fused state may be applied if needed. This method enables preparation of an adhesive having physical parameters according to the present invention.

Mixing with stirring is not particularly limited, and may be carried out from initiation of the fusion until the fused state is reached. The temperature during mixing with stirring is preferably no less than 50° C. The stirring is preferably conducted concurrently with shear loading. In this case, stirring speed is preferably no less than 50 rpm, and more preferably no less than 100 rpm.

The apparatus used for mixing by stirring may be, for example, a Henschel mixer (registered trade name), a kneader, an open roll, a mixing roll, an internal mixer, a banbury mixer, a plast mill, a biaxial kneader, an extrusion kneader, or the like. Among these, in light of ease in stirring at a high speed, a Henschel mixer (registered trade name) is preferred.

Production of Skin Patch (Plaster)

The thickness of the adhesive layer applied on the backing of the skin patch of the present invention is preferably 90 μm to 250 μm. When the thickness of the adhesive layer is too great, it is likely to be stripped during use as a result of contact of a corner thereof with clothes or the like. In contrast, when the thickness is too small, supportive properties provided to the skin patch may be lost, and thus errors in application are likely to result.

The method of manufacturing the skin patch of the present invention is not limited to the procedures as described above, and the temperature conditions, rate of stirring, stirring time and the like may be regulated depending on the machine used for production, production scale, and the like.

According to this method of manufacture, an adhesive having a tan δ value, which was determined by measurement of dynamic viscoelasticity at 32° C., that satisfies the following formula 1 on at least one point in the region of the frequency being no less than 0.04 Hz and no greater than 0.25 Hz as described later can be readily produced.

$$0.25x+0.05 \leq y \leq 0.25x+0.10 \qquad \text{Formula 1}$$

(Herein, x represents a frequency (Hz), and y represents tan δ.)

Measurement of Tan δ

Tan δ is a physical characteristic value derived from dynamic loss modulus (G") and storage modulus of elasticity (dynamic shear modulus) (G').

$$\tan \delta = G''/G'$$

The measurement of tan δ may be carried out according to the following procedures using, for example, Rheometric Dynamic Analyzer as an apparatus for the measurement.

First, the adhesive is scraped from the skin patch, and then from 50 mg to 75 mg of the adhesive is sandwiched in a cylindrical jig in the aforementioned apparatus. Next, the stress generated when a strain is applied while increasing the frequency from 0.01 Hz to 80 Hz with a common ratio of 1.259 Hz at 32° C. is detected. Based on the results of the detected value, the dynamic loss modulus (G") and the storage modulus of elasticity (dynamic shear modulus) (G') are calculated to determined the tan δ value.

The adhesive that constitutes the skin patch of the present invention has a tan δ value, which was determined by measurement of dynamic viscoelasticity at 32° C., that satisfies the following formula 1 on at least one point in a range of frequency of 0.04 Hz to 0.25 Hz.

$$0.25x+0.05 \leq y \leq 0.25x+0.10 \qquad \text{Formula 1}$$

(Herein, x represents a frequency (Hz), and y represents tan δ.)

The tan δ value determined by measurement of dynamic viscoelasticity at 32° C. preferably satisfies the formula 1 on an arbitrary point in the region of the frequency being no less than 0.04 Hz and no greater than 0.25 Hz since handleability can be further improved, and the irritation that a user experiences can be further reduced. It should be noted that the phrase "an arbitrary point in the region of the frequency being no less than 0.04 Hz and no greater than 0.25 Hz" refers to all possible points of the measurement in the region of the frequency being no less than 0.04 Hz and no greater than 0.25 Hz, and the number of all possible points of the measurement is not particularly limited.

The adhesive that constitutes the skin patch of the present invention has a tan δ value, which was determined by measurement of dynamic viscoelasticity at 32° C., that satisfies the following formula 2 on at least one point in a range of frequency of 0.04 Hz to 0.10 Hz.

$$0.25x+0.05 \leq y \leq 0.65x+0.09 \qquad \text{Formula 2}$$

(Herein, x represents a frequency (Hz), and y represents tan δ.)

The adhesive that constitutes the skin patch of the present invention has a tan δ value, which was determined by measurement of dynamic viscoelasticity at 32° C., that satisfies more preferably the following formula 3 or 4, and still more preferably the formula 5, on at least one point in a range of frequency of 0.04 Hz to 0.10 Hz.

$$0.25x+0.05 \leq y \leq 0.25x+0.10 \qquad \text{Formula 3}$$

$$0.35x+0.04 \leq y \leq 0.65x+0.09 \qquad \text{Formula 4}$$

$$0.35x+0.04 \leq y \leq 0.25x+0.10 \qquad \text{Formula 5}$$

(Herein, x represents a frequency (Hz), and y represents tan δ.)

The tan δ value determined by measurement of dynamic viscoelasticity at 32° C. preferably satisfies any of the formulae 2 to 5 on an arbitrary point in a range of frequency of 0.04 Hz to 0.10 Hz, since handleability can be further improved and the irritation that a user experiences can be further reduced. It should be noted that the phrase "an arbitrary point in a range of frequency of 0.04 Hz to 0.10 Hz" refers to all possible points of measurement in a range of frequency of 0.04 Hz to 0.10 Hz, and the number of all possible points of the measurement is not particularly limited.

In addition, from another perspective, the adhesive has a tan δ value obtained by measurement of dynamic viscoelasticity at 32° C. and at a frequency of 0.10 Hz that is no less than 0.065 and no greater than 0.165, preferably no less than 0.075 and no greater than 0.155, and more preferably no less than 0.079 and no greater than 0.154.

From yet another perspective, the adhesive has a tan δ value determined by measurement of dynamic viscoelasticity at 32° C. and at a frequency of 0.05 Hz that is no less than 0.053 and no greater than 0.150, preferably no less than 0.0625 and no greater than 0.143, and more preferably no less than 0.0625 and no greater than 0.113.

For reference, the temperature of 32° C. is an average temperature of human superficial skin to which a skin patch is generally applied. Thus, a tan δ value determined by measurement of dynamic viscoelasticity at 32° C. is assumed to reflect characteristics of skin patches in use. Therefore, when the temperature of the subject to which the skin patch is applied varies, the skin patch can be evaluated based on the tan δ value determined by measurement of dynamic viscoelasticity of the adhesive layer at the temperature. Accordingly, the "temperature of the subject to which the skin patch is applied" may be defined to meet the application and the like of the skin patch.

The adhesive that constitutes the skin patch of the present invention has a glass transition temperature (Tg) of preferably no less than −45° C. and no greater than −35° C., and more preferably no less than −43° C. and no greater than −35° C.

EXAMPLES

Next, the present invention will be specifically explained by way of Examples, but the present invention is not in any way limited thereto.

Example 1

Into a Henschel mixer (registered trade name, manufactured by Nippon Coke & Engineering Co., Ltd.,) 4162.5 g of liquid paraffin (MORESCO WHITE P-350P; manufactured by Matsumura Oil Research Corp.) as a plasticizer, 22.5 g of dibutylhydroxytoluene as an anti-oxidizing agent, 2250 g of a pre-heated "Ester Gum H (trade name)" (manufactured by Arakawa Chemical Industries, Ltd.) as a tackifier, were added and mixed at 200 rpm and a temperature of 100° C.

To this mixture 2250 g of an SIS block copolymer (D-KX401CS; manufactured by Kraton JSR Elastomers K.K.) having a mass ratio of styrene to isoprene (styrene/isoprene) being 22/78, was added and the mixture was dissolved by raising the temperature to 190° C. while shearing under a condition at a shearing speed of 900 rpm and a temperature of 190° C.

Then, the resulting solution was stirred while shearing at 900 rpm for 20 min. To the stirred mixture, 135 g of l-menthol and 180 g of N-methyl-2-pyrrolidone as a drug solubilizer and/or a transdermal absorption-promoting agent were added, followed by mixing with stirring to prepare an adhesive.

Subsequently, the resulting adhesive was applied to a knit (made with polyester), having a mass per unit area of 100 g/m², to a thickness of 150 μm. A skin patch (plaster) was produced by laminating on the adhesive a liner (made of PET) which had been subjected to silicon treatment.

Example 2

A skin patch (plaster) was produced by preparing an adhesive by a similar procedure to Example 1, except that: the amount of liquid paraffin added was 3870 g; the amount of l-menthol added was 270 g; the amount of dibutylhydroxytoluene added was 90 g; and 90 g of diclofenac sodium was further added.

Example 3

A skin patch (plaster) was produced by preparing an adhesive by a similar procedure to Example 2, except that: ketoprofen was added in place of diclofenac sodium; and "KE-100 (trade name)" was added in place of "Ester Gum H (trade name)".

Example 4

A skin patch (plaster) was produced by preparing an adhesive by a similar procedure to Example 3, except that: the amount of liquid paraffin added was 3847.5 g; the amount of dibutylhydroxytoluene added was 112.5 g; and "Ester Gum H (trade name)" was used in place of "KE-100 (trade name)".

Example 5

A skin patch (plaster) was produced by preparing an adhesive by a similar procedure to Example 1, except that: the amount of liquid paraffin added was 3856.5 g; the amount of N-methyl-2-pyrrolidone added was 360 g; "KE-100 (trade name)" was used in place of "Ester Gum H (trade name)"; and 90 g of indometacin and 36 g of citric acid were further added.

Example 6

A skin patch (plaster) was produced by preparing an adhesive by a similar procedure to Example 5, except that: the amount of liquid paraffin added was 3654 g; the amount of dibutylhydroxytoluene added was 45 g; 180 g of a hydrogenated oil was further added; and diclofenac sodium was added in place of indometacin.

Example 7

A skin patch (plaster) was produced by preparing an adhesive by a similar procedure to Example 1, except that: the amount of "D-KX401CS (trade name)" added was 3150 g; the amount of "Ester Gum H (trade name)" added was 2700 g; the amount of liquid paraffin added was 3150 g; and further, N-methyl-2-pyrrolidone, 1-menthol and dibutylhydroxytoluene were not added.

Example 8

A skin patch (plaster) was produced by preparing an adhesive by a similar procedure to Example 1, except that: the amount of "D-KX401CS (trade name)" added was 1800 g; the amount of liquid paraffin added was 3510 g; the amount of l-menthol added was 90 g; 180 g of a hydrogenated oil and 90 g of felbinac were further added; dibutylhydroxytoluene was not added; and 3510 g of "KE-100 (trade name)" was added in place of "Ester Gum H (trade name)".

Example 9

A skin patch (plaster) was produced by preparing an adhesive by a similar procedure to Example 1, except that: the amount of "D-KX401CS (trade name)" added was 1350 g; the amount of "Ester Gum H (trade name)" added was 2700 g; the amount of liquid paraffin added was 3960 g; 900 g of an SIS block copolymer (D-1107; manufactured by Kraton JSR Elastomers K.K.) having a mass ratio of styrene to isoprene (styrene/isoprene) being 15/85 and 90 g of ketoprofen were further added; and N-methyl-2-pyrrolidone, 1-menthol, and dibutylhydroxytoluene were not added.

Example 10

A skin patch (plaster) was produced by preparing an adhesive by a similar procedure to Example 6, except that: the amount of "D-KX401CS (trade name)" added was 2700 g; the amount of liquid paraffin added was 3127.5 g; the amount of N-methyl-2-pyrrolidone added was 450 g; the amount of dibutylhydroxytoluene added was 22.5 g; and the amount of citric acid added was 45 g.

Comparative Example 1

A skin patch (plaster) was produced by preparing an adhesive by a similar procedure to Example 3, except that: the amount of N-methyl-2-pyrrolidone added was 270 g; "D-1107 (trade name)" was added in place of "D-KX401CS (trade name)"; and ketoprofen was not added.

Comparative Example 2

A skin patch (plaster) was produced by preparing an adhesive by a similar procedure to Example 2, except that: the amount of liquid paraffin added was 3780 g; the amount of N-methyl-2-pyrrolidone added was 270 g; and "D-1107 (trade name)" was added in place of "D-KX401CS (trade name)".

A summary of the compositions of Examples 1 to 10 and Comparative Examples 1 to 2 are as shown in Table 1.

TABLE 1

| | SIS | Tackifier | LP | Hydrogenated oil | Optional Ingredient | | | | Medicinal Agent |
|---|---|---|---|---|---|---|---|---|---|
| | | | | | Solubilizer and Transdermal Absorption Promoting Agent of Drug | | | | |
| | | | | | NMP | L-MEN | BHT | Others | |
| Example 1 | 22/78 2250 g | EGH 2250 g | 4162.5 g | — | 180 g | 135 g | 22.5 g | — | — |
| Example 2 | 22/78 2250 g | EGH 2250 g | 3870 g | — | 180 g | 270 g | 90 g | — | DFNa 90 g |
| Example 3 | 22/78 2250 g | KE 2250 g | 3870 g | — | 180 g | 270 g | 90 g | — | KP 90 g |
| Example 4 | 22/78 2250 g | EGH 2250 g | 3847.5 g | — | 180 g | 270 g | 112.5 g | — | KP 90 g |
| Example 5 | 22/78 2250 g | KE 2250 g | 3856.5 g | — | 360 g | 135 g | 22.5 g | Citric Acid 36 g | ID 90 g |
| Example 6 | 22/78 2250 g | KE 2250 g | 3654 g | 180 g | 360 g | 135 g | 45 g | Citric Acid 36 g | DFNa 90 g |
| Example 7 | 22/78 3150 g | EGH 2700 g | 3150 g | — | — | — | — | — | — |
| Example 8 | 22/78 1800 g | KE 3150 g | 3510 g | 180 g | 180 g | 90 g | — | — | FB 90 g |
| Example 9 | 22/78 1350 g 15/85 900 g | EGH 2700 g | 3960 g | — | — | — | — | — | KP 90 g |
| Example 10 | 22/78 2700 g | KE 2250 g | 3127.5 g | 180 g | 450 g | 135 g | 22.5 g | Citric Acid 45 g | DFNa 90 g |
| Comparative Example 1 | 15/85 2250 g | KE 2250 g | 3870 g | — | 270 g | 270 g | 90 g | — | — |
| Comparative Example 2 | 15/85 2250 g | EGH 2250 g | 3780 g | — | 270 g | 270 g | 90 g | — | DFNa 90 g |

SIS: SIS block copolymer
EGH: Ester Gum H (rosin ester derivative)
KE: KE-100 (rosin ester derivative)
BHT: dibutylhydroxytoluene
LP: liquid paraffin
NMP: N-methyl-2-pyrrolidone
L-MEN: l-menthol
KP: ketoprofen
DFNa: diclofenac sodium
ID: indometacin
FB: felbinac Examples 1 to 10, Comparative Examples 1 to 2, and commercially available skin patches a to g containing an SIS adhesive were evaluated based on self-adhesion property (handleability), skin irritation property, adhesion to skin, and adhesion to skin in the presence of moisture (water resistance), by measuring a physical characteristic value (tan δ) of the adhesive. Commercially available products are, respectively, commercial product a: "MOHRUS tape" (manufactured by Hisamitsu Pharmaceutical Co., Inc.); commercial product b: "YAKUBAN" (manufactured by TOKUHON Corporation); commercial product c: "Flex" (manufactured by Hisamitsu Pharmaceutical Co., Inc.); commercial product d: "Falken" (manufactured by Yutoku Pharmaceutical Ind. Co., Ltd.); commercial product e: "Rheila tape" (manufactured by Teikoku Medix Co., Ltd.); commercial product f "Voltaren tape": (manufactured by Novartis Pharma K.K.); and commercial product g: "KETOTAX" (manufactured by Toko Pharmaceutical Industrial Co., Ltd.).

Test Example 1

Measurement of Tan δ

Using a rheometric dynamic analyzer "Dynamic Analyzer RDAIII (trade name)" (manufactured by Rheometric Scientific, Inc.), the storage elastic modulus (G') and the like of the adhesive were determined.

Specifically, the adhesive was first scraped from the adhesive layer of each skin patch, and then about 65 mg of the adhesive was sandwiched in a cylindrical jig. The stress generated when a strain of 1% was applied to the adhesive while increasing the frequency from 0.01 Hz to 80 Hz at a common ratio of 1.259 Hz at 32° C. was plotted every 12 sec. Parallel plates having a diameter of 25 mm were used and the clearance (Gap) was set to be 1.2 mm. G' and G" were calculated using PC software (Orchestrator Ver. 6.5.6; produced by Rheometric Scientific, Inc.). Tan δ (=G"/G') was similarly calculated using PC software (Orchestrator Ver. 6.5.6; produced by Rheometric Scientific, Inc.).

Measurement Condition

Frequency: 0.01 to 80 Hz (increased at a common ratio of 1.259 Hz)
Temperature: 32° C.
Plot of measurement: measured and plotted every 12 sec
Plate: parallel plates with a diameter of 25 mm
Clearance (Gap): 1.2 mm
Amount of strain: 1%

Figure 1:
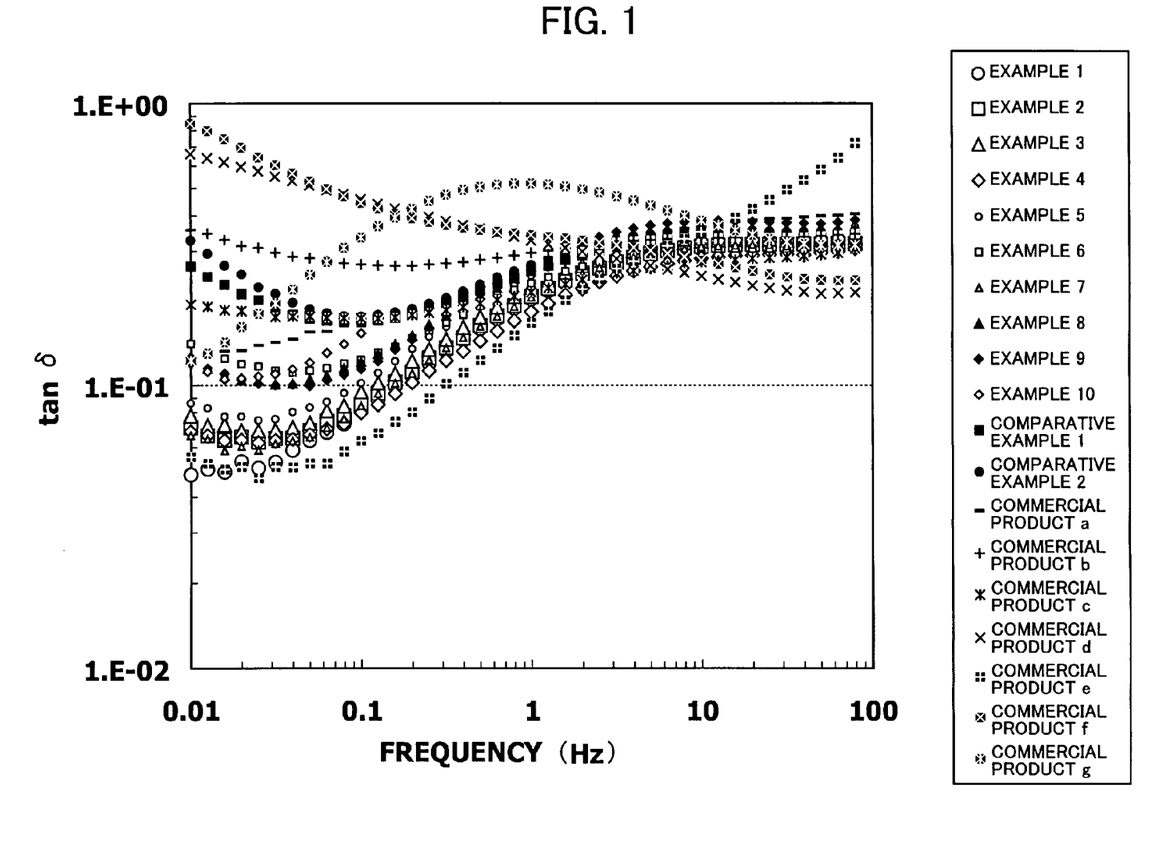
FIG. 1 is a graph showing relationships between frequency and tan δ in skin patches according to examples of the present invention.
Figure 2:
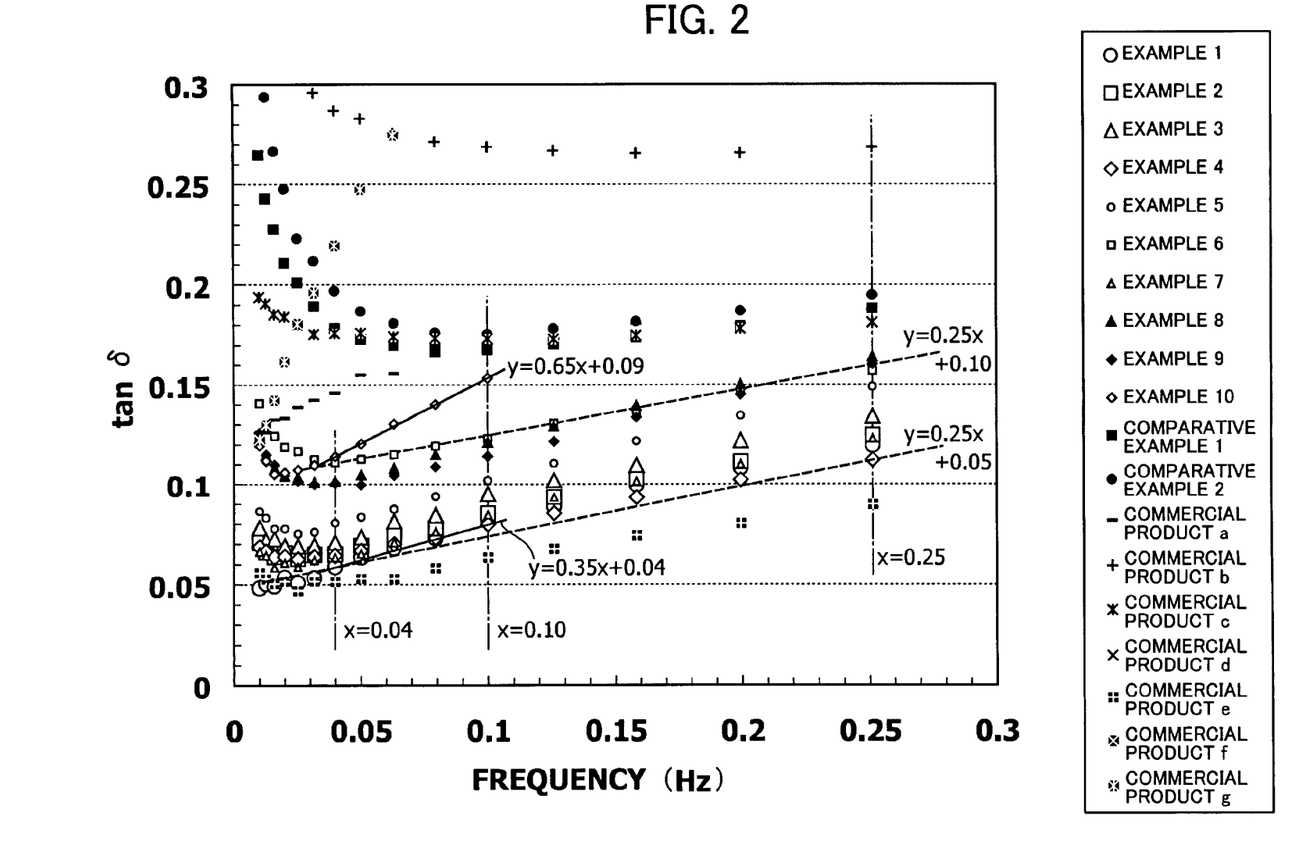
FIG. 2 is a graph showing relationships between frequency in a specified region and tan δ in skin patches according to examples of the present invention.

Measurement was carried out using the adhesives obtained in Examples 1 to 10, and Comparative Examples 1 to 2, and the adhesives included in the commercial products a to g. Tan δ values of these samples at 32° C. are shown in Table 2. Furthermore, the relationship between the frequency and tan δ are shown in FIG. 1 and FIG. 2 as graphical representations. It should be noted that FIG. 1 is a graph showing the relationship between the frequency in the entire region of 0.01 to 80 Hz, and tan δ displayed on a logarithmic scale, and that FIG. 2 is a graph showing a partially enlarged portion in the region of the frequency being 0 to 0.30 Hz.

TABLE 2

| frequency (Hz) | Example 1 | Example 2 | Example 3 | Example 4 | Example 5 | Example 6 | Example 7 | Example 8 | Example 9 | Example 10 | Comparative Example 1 |
|---|---|---|---|---|---|---|---|---|---|---|---|
| 0.01 | 0.04815 | 0.07061 | 0.07804 | 0.06844 | 0.0863 | 0.14064 | 0.06929 | 0.12319 | 0.12598 | 0.11946 | 0.26456 |
| 0.01259 | 0.05033 | 0.06612 | 0.07184 | 0.06528 | 0.08295 | 0.12961 | 0.06283 | 0.11464 | 0.11478 | 0.11178 | 0.2428 |
| 0.01585 | 0.04922 | 0.06378 | 0.07244 | 0.06356 | 0.07759 | 0.12417 | 0.06231 | 0.10793 | 0.10977 | 0.10495 | 0.22762 |
| 0.01995 | 0.05354 | 0.06539 | 0.06894 | 0.06378 | 0.07749 | 0.11868 | 0.06296 | 0.10414 | 0.10447 | 0.10589 | 0.21068 |
| 0.02512 | 0.05079 | 0.06275 | 0.06885 | 0.06244 | 0.07502 | 0.11661 | 0.06186 | 0.10348 | 0.10131 | 0.10724 | 0.20099 |
| 0.03162 | 0.05323 | 0.06469 | 0.0693 | 0.06356 | 0.0759 | 0.11234 | 0.05991 | 0.10078 | 0.09986 | 0.10951 | 0.18921 |
| 0.03981 | 0.05872 | 0.06485 | 0.07077 | 0.06417 | 0.08035 | 0.11076 | 0.06206 | 0.10134 | 0.10032 | 0.11389 | 0.17804 |
| 0.05012 | 0.06345 | 0.06901 | 0.07335 | 0.06667 | 0.08336 | 0.11247 | 0.06675 | 0.1047 | 0.09944 | 0.1203 | 0.17268 |
| 0.0631 | 0.06789 | 0.0744 | 0.08121 | 0.06994 | 0.08731 | 0.11484 | 0.07408 | 0.10794 | 0.10429 | 0.13022 | 0.1696 |
| 0.07943 | 0.07277 | 0.0778 | 0.08438 | 0.07304 | 0.09364 | 0.11924 | 0.07934 | 0.1149 | 0.10876 | 0.14004 | 0.16778 |
| 0.1 | 0.08167 | 0.08505 | 0.0948 | 0.07976 | 0.10178 | 0.12289 | 0.08594 | 0.12106 | 0.11401 | 0.15334 | 0.16766 |
| 0.12589 | 0.08868 | 0.09334 | 0.10187 | 0.08526 | 0.11039 | 0.1306 | 0.0928 | 0.12916 | 0.12152 | — | 0.17025 |
| 0.15849 | 0.09944 | 0.10233 | 0.10959 | 0.09316 | 0.1218 | 0.13682 | 0.10287 | 0.13955 | 0.13369 | — | 0.17382 |
| 0.19953 | 0.10828 | 0.11125 | 0.122 | 0.10215 | 0.13449 | 0.14712 | 0.11147 | 0.15009 | 0.14517 | — | 0.17926 |
| 0.25119 | 0.11961 | 0.12461 | 0.13407 | 0.11231 | 0.14905 | 0.15683 | 0.12503 | 0.16417 | 0.16021 | — | 0.18814 |
| 0.31623 | 0.1326 | 0.13577 | 0.14562 | 0.12246 | 0.16153 | 0.1672 | 0.13657 | 0.17642 | 0.17744 | — | 0.19565 |
| 0.39811 | 0.1451 | 0.14709 | 0.16079 | 0.13212 | 0.17841 | 0.17813 | 0.15021 | 0.19077 | 0.19273 | — | 0.2055 |
| 0.50119 | 0.15938 | 0.16293 | 0.175 | 0.14364 | 0.19405 | 0.19116 | 0.16378 | 0.2076 | 0.21132 | — | 0.21689 |
| 0.63096 | 0.17245 | 0.17623 | 0.18995 | 0.1558 | 0.21157 | 0.20329 | 0.17794 | 0.22175 | 0.22912 | — | 0.22875 |
| 0.79433 | 0.18786 | 0.19155 | 0.20659 | 0.16953 | 0.22787 | 0.21775 | 0.19271 | 0.2395 | 0.24796 | — | 0.2408 |
| 1 | 0.20254 | 0.20632 | 0.22259 | 0.18258 | 0.245 | 0.22941 | 0.20691 | 0.25447 | 0.26679 | — | 0.25412 |
| 1.25893 | 0.21723 | 0.22041 | 0.23631 | 0.19494 | 0.26247 | 0.2415 | 0.22212 | 0.26976 | 0.28615 | — | 0.26568 |
| 1.58489 | 0.23204 | 0.23603 | 0.25206 | 0.20914 | 0.27881 | 0.25383 | 0.23781 | 0.28427 | 0.3039 | — | 0.27788 |
| 1.99526 | 0.24558 | 0.24973 | 0.26612 | 0.22097 | 0.29268 | 0.26407 | 0.25063 | 0.29815 | 0.32093 | — | 0.28949 |
| 2.51189 | 0.25751 | 0.26052 | 0.27777 | 0.23282 | 0.30568 | 0.27356 | 0.26355 | 0.30968 | 0.33603 | — | 0.29978 |
| 3.16228 | 0.2694 | 0.27399 | 0.29083 | 0.24449 | 0.31944 | 0.28268 | 0.27584 | 0.32039 | 0.34965 | — | 0.30989 |
| 3.98108 | 0.27994 | 0.28401 | 0.30093 | 0.25503 | 0.32897 | 0.29044 | 0.28608 | 0.32961 | 0.36087 | — | 0.31774 |
| 5.01188 | 0.28756 | 0.29341 | 0.30918 | 0.26371 | 0.33704 | 0.29616 | 0.29076 | 0.33643 | 0.37021 | — | 0.32436 |
| 6.30958 | 0.29591 | 0.30064 | 0.3164 | 0.27077 | 0.34299 | 0.30056 | 0.30259 | 0.34236 | 0.37641 | — | 0.32887 |
| 7.94329 | 0.30109 | 0.30736 | 0.32143 | 0.27747 | 0.34725 | 0.3035 | 0.30764 | 0.34518 | 0.38092 | — | 0.33245 |

| frequency (Hz) | Comparative Example 2 | Commercial Product a | Commercial Product b | Commercial Product c | Commercial Product d | Commercial Product e | Commercial Product f | Commercial Product g |
|---|---|---|---|---|---|---|---|---|
| 0.01 | 0.32701 | 0.126 | 0.35564 | 0.19389 | 0.66057 | 0.05571 | 0.84556 | 0.12248 |
| 0.01259 | 0.29371 | 0.12623 | 0.34562 | 0.19072 | 0.6391 | 0.05276 | 0.79714 | 0.12998 |
| 0.01585 | 0.2665 | 0.1323 | 0.32804 | 0.18523 | 0.61805 | 0.05027 | 0.74629 | 0.14216 |
| 0.01995 | 0.24761 | 0.13308 | 0.31244 | 0.18385 | 0.59479 | 0.05136 | 0.69498 | 0.16154 |
| 0.02512 | 0.22299 | 0.13866 | 0.30784 | 0.18009 | 0.5743 | 0.04678 | 0.64211 | 0.18034 |
| 0.03162 | 0.21171 | 0.14231 | 0.29583 | 0.1753 | 0.54907 | 0.05138 | 0.60455 | 0.19599 |
| 0.03981 | 0.19682 | 0.14582 | 0.28671 | 0.17565 | 0.5301 | 0.05125 | 0.5632 | 0.21934 |
| 0.05012 | 0.18678 | 0.15479 | 0.28276 | 0.17578 | 0.51088 | 0.05278 | 0.52781 | 0.24731 |
| 0.0631 | 0.18079 | 0.15542 | 0.27549 | 0.17401 | 0.49204 | 0.05275 | 0.49684 | 0.27444 |
| 0.07943 | 0.17609 | 0.16458 | 0.27126 | 0.17332 | 0.47524 | 0.05816 | 0.46825 | 0.30791 |
| 0.1 | 0.17541 | 0.17065 | 0.26869 | 0.17304 | 0.4564 | 0.06336 | 0.44417 | 0.335 |
| 0.12589 | 0.17804 | 0.1733 | 0.26676 | 0.17286 | 0.43953 | 0.06749 | 0.42436 | 0.36673 |
| 0.15849 | 0.18167 | 0.18049 | 0.26547 | 0.17472 | 0.4238 | 0.07419 | 0.40538 | 0.39415 |
| 0.19953 | 0.18696 | 0.18686 | 0.26562 | 0.17796 | 0.41049 | 0.08015 | 0.3922 | 0.42261 |
| 0.25119 | 0.19475 | 0.19458 | 0.26851 | 0.18114 | 0.39656 | 0.08971 | 0.38022 | 0.45124 |
| 0.31623 | 0.20449 | 0.20369 | 0.27078 | 0.18531 | 0.3828 | 0.10106 | 0.37078 | 0.4739 |
| 0.39811 | 0.21581 | 0.21326 | 0.27408 | 0.18967 | 0.37002 | 0.11068 | 0.363 | 0.49248 |
| 0.50119 | 0.22766 | 0.22333 | 0.27951 | 0.19558 | 0.3593 | 0.12252 | 0.35659 | 0.50505 |
| 0.63096 | 0.24143 | 0.23305 | 0.28368 | 0.20111 | 0.34694 | 0.13553 | 0.3509 | 0.51486 |
| 0.79433 | 0.25423 | 0.24422 | 0.28909 | 0.20725 | 0.3365 | 0.15044 | 0.34655 | 0.51951 |
| 1 | 0.26798 | 0.25537 | 0.29559 | 0.21372 | 0.32626 | 0.16671 | 0.34144 | 0.51962 |
| 1.25893 | 0.28179 | 0.2665 | 0.30055 | 0.22146 | 0.31665 | 0.18347 | 0.33654 | 0.51525 |
| 1.58489 | 0.29542 | 0.27957 | 0.30678 | 0.22813 | 0.30742 | 0.20104 | 0.33224 | 0.50632 |
| 1.99526 | 0.30792 | 0.29211 | 0.31187 | 0.23698 | 0.29846 | 0.21952 | 0.32633 | 0.49541 |
| 2.51189 | 0.31953 | 0.30466 | 0.31649 | 0.24184 | 0.28974 | 0.23802 | 0.3208 | 0.48204 |
| 3.16228 | 0.32957 | 0.31777 | 0.32145 | 0.24899 | 0.28174 | 0.25931 | 0.31466 | 0.46791 |
| 3.98108 | 0.3383 | 0.32902 | 0.32505 | 0.25539 | 0.27337 | 0.27627 | 0.30852 | 0.45203 |
| 5.01188 | 0.3448 | 0.34074 | 0.32766 | 0.26146 | 0.26613 | 0.29338 | 0.30121 | 0.43555 |
| 6.30958 | 0.35026 | 0.35111 | 0.33017 | 0.26656 | 0.25835 | 0.31278 | 0.29408 | 0.41787 |
| 7.94329 | 0.35347 | 0.35956 | 0.33245 | 0.27056 | 0.25103 | 0.33084 | 0.28621 | 0.40099 |

Test Example 2

Evaluation of Handleability

After peeling the liner of the skin patch, the adhesive layer face of each of the aforementioned commercial products a to g, and the skin patches (10 cm×7 cm) of Examples 1 to 10 and Comparative Examples 1 to 2 were folded in half so that the two halves were in contact with each other. Sensory evaluation was conducted for the ease of release in peeling based on the following standards.
Evaluation Standards
  A: separable without resistance
  B: separable accompanied by some resistance
  C: separable with some degree of difficulty
  D: separable with difficulty in returning to the original state, accompanied by partial detachment of the adhesive layer Test Example 3

Evaluation of Skin Irritation Property (Pain in Peeling)

The commercial products a to g, and the skin patches (10 cm×7 cm) of Examples 1 to 10 and Comparative Examples 1 to 2 were applied to an area on the right upper arm of five monitors. The pain felt upon peeling each skin patch from the area on the right upper arm was evaluated according to the following standards.
Evaluation Standards
  A: no pain felt at all.
  B: some pain felt.
  C: pain felt.
  D: strong pain felt.

Test Example 4

Evaluation of Adhesion to Skin

The commercial products a to g, and the skin patches (10 cm×7 cm) of Examples 1 to 10 and Comparative Examples 1 to 2 were applied to an area on the right upper arm of five monitors. The state of application (state of detachment) on the skin of each skin patch after 8 hours was visually observed. The skin patches with their entire face attached to the skin were deemed as "no release", and evaluation was made according to the following standards.
Evaluation Standards
  A: no release
  B: very slight release
  C: relatively broad release on any of the four corners and the like
  D: release found over a wide area, or considerable shift found in the application site Test Example 5

Evaluation of Adhesion to Skin in the Presence of Moisture (Water Resistance)

The commercial products a to g, and the skin patches (10 cm×7 cm) of Examples 1 to 10 and Comparative Examples 1 to 2 were applied to an area on the right upper arm of five monitors after spraying purified water on the respective areas, followed by employing the test procedure according to Test Example 4 to evaluate the adhesion to skin of each skin patch.
Results of evaluation by Test Examples 2 to 5 are shown in Table 3.

TABLE 3

|  | Test Example 2 Handleability | Test Example 3 Pain in Peeling | Test Example 4 Adhesion to Skin | Test Example 5 Adhesion to Skin in the Presence of Moisture |
|---|---|---|---|---|
| Commercial Product a | C | D | A | B |
| Commercial Product b | C | D | A | — |
| Commercial Product c | B | C | A | — |
| Commercial Product d | D | — | B | — |
| Commercial Product e | C | — | B | — |
| Commercial Product f | D | C | C | D |
| Commercial Product g | C | C | D | — |
| Example 1 | A | A | A | A |
| Example 2 | A | A | A | A |
| Example 3 | A | A | A | A |
| Example 4 | A | A | A | A |
| Example 5 | A | A | A | A |
| Example 6 | A | A | A | A |
| Example 7 | A | A | A | A |
| Example 8 | A | A | A | A |
| Example 9 | A | A | A | A |
| Example 10 | A | A | A | A |
| Comparative Example 1 | C | B | A | A |
| Comparative Example 2 | C | B | A | A |

As shown in Table 2 and FIGS. 1 to 2, any of the adhesives produced in Examples 1 to 9 had a tan δ value, which was determined by measurement of dynamic viscoelasticity at 32° C., that satisfied the formula 1 on an arbitrary point in a range of frequency of 0.04 Hz to 0.25 Hz. To the contrary, none of the commercial products a to g and the adhesives produced in Comparative Examples 1 to 2 had a tan δ value, which was determined by measurement of dynamic viscoelasticity at 32° C., that satisfied the formula 1 on any point in a range of frequency of 0.04 Hz to 0.25 Hz.

Moreover, any of the adhesives produced in Examples 1 to 10 had a tan δ value, which was determined by measurement of dynamic viscoelasticity at 32° C., that satisfied the formula 2 on an arbitrary point in a range of frequency of 0.04 Hz to 0.10 Hz. To the contrary, none of the commercial products a to g and the adhesives produced in Comparative Examples 1 to 2 had a tan δ value, which was determined by measurement of dynamic viscoelasticity at 32° C., that satisfied the formula 2 on any point in a range of frequency of 0.04 Hz to 0.10 Hz.

On the other hand, as shown in Table 3, it was demonstrated that the skin patches produced in Examples 1 to 10 could improve the handleability, adhesion to skin, and water resistance, furthermore the amount of irritation caused to the skin could be reduced. In contrast, none of the commercial products "a" to "g" and skin patches produced in Comparative Examples 1 to 2 could improve the handleability, adhesion to skin, and water resistance; furthermore, the amount of irritation caused to the skin could not be reduced.

Test Example 6

Evaluation of Handleability

After pressure-sensitive adhesive tape (gum tape) was adhered onto the backing side face of the skin patch of Example 6, as well as commercial products a and f to reinforce each skin patch, a plurality of pieces were then obtained by cutting each patch to give a width of 2.5 cm. Next, after the release liner was peeled from each test piece, the adhesive layer faces were brought into contact with each other, and pressure bonding was performed by making one back-and-forth motion thereon with a 2-kg roller. Subsequently, a pull tab was formed with the gum tape to complete production of the test piece. This test piece was pinched with upper and lower clamps of a tensile testing machine, and the test piece was peeled at a rate of 300 mm/min, and a load required for completely peeling was measured. The measurement was carried out three times, and the average value of the measured load was determined. The results are shown in FIG. 3.

Figure 3:
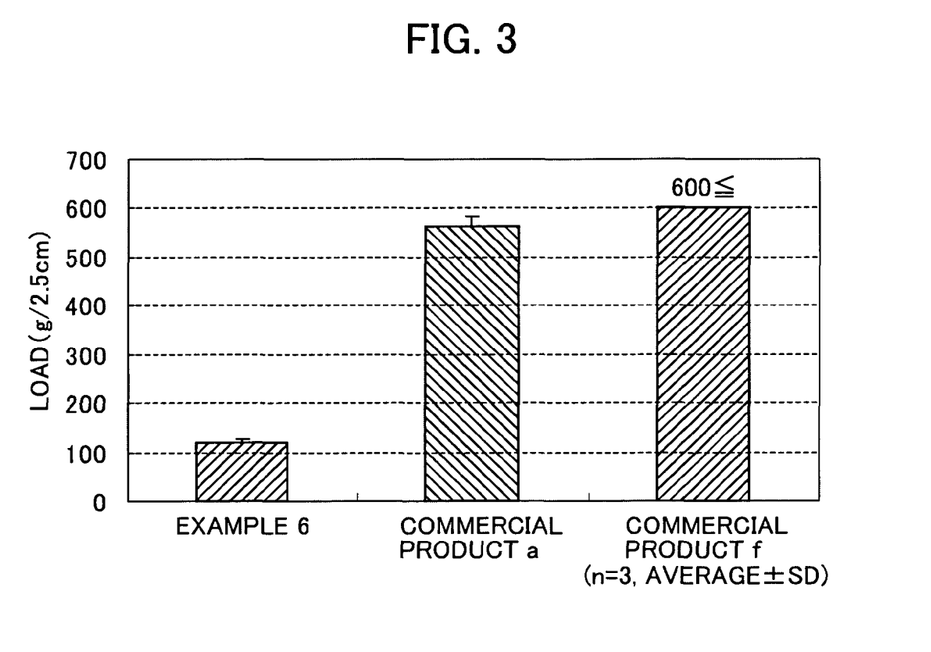
FIG. 3 is a graph showing an average load required for peeling off a skin patch according to one example of the present invention during self-adhesion.

As shown in FIG. 3, the skin patch produced in Example 6 was peeled with a significantly smaller load as compared with the commercial products a and f. Accordingly, it was proven that the skin patch produced in Example 6 could be readily peeled in the case of self-adhesion, and thus the handleability could be improved.

From the foregoing, it was revealed that by allowing the adhesive containing an SIS block copolymer to have a tan δ value, which was determined by measurement of dynamic viscoelasticity at 32° C., that satisfies the formula 1 in a range of frequency of 0.04 Hz to 0.25 Hz, superior adhesion to skin was provided, while the handleability and water resistance could be improved, and the irritation that a user experiences could be reduced.

In addition, it was revealed that by allowing the adhesive containing an SIS block copolymer to have a tan δ value, which was determined by measurement of dynamic viscoelasticity at 32° C., that satisfies the formula 2 in a range of frequency of 0.04 Hz to 0.10 Hz, superior adhesion to skin was provided, while the handleability and water resistance could be improved, and the irritation that a user experiences could be reduced.

The above results, when estimated from another perspective, suggest that adhesion to skin, handleability and water resistance of skin patches in use, as well as irritation that a user experiences, can be evaluated adequately, on the basis of a tan δ value determined by measurement of dynamic viscoelasticity of the adhesive layer at 32° C., which is an average temperature of human superficial skin to which a skin patch is typically applied.

The invention claimed is:

1. A skin patch comprising a flexible backing, and an adhesive layer laminated on the backing,
   wherein the adhesive layer comprises a styrene-isoprene-styrene block copolymer, and has a tan δ value, determined by measurement of dynamic viscoelasticity at 32° C., that satisfies the following formula 1 on at least one point in a range of frequency of 0.04 Hz to 0.25 Hz:

$$0.25x+0.05 \leq y \leq 0.25x+0.10 \qquad \text{Formula 1}$$

wherein, x represents a frequency (Hz) and y represents tan δ.

2. The skin patch according to claim 1, wherein the tan δ value determined by measurement of dynamic viscoelasticity at 32° C. satisfies the above formula 1 on an arbitrary point in a range of frequency of 0.04 Hz to 0.25 Hz.

3. The skin patch according to claim 1, wherein the adhesive layer further comprises:
   a tackifier; and a plasticizer.

4. The skin patch according to claim 3, wherein the content of the styrene-isoprene-styrene block copolymer is no less than 10% by mass and no greater than 40% by mass; the content of the tackifier is no less than 10% by mass and no greater than 35% by mass; and the content of the plasticizer is no less than 20% by mass and no greater than 60% by mass based on the mass of the entire adhesive layer.

5. The skin patch according to claim 1, wherein the styrene-isoprene-styrene block copolymer has a mass ratio of styrene to isoprene (styrene/isoprene) of no less than 20/80 and no greater than 25/75.

6. The skin patch according to claim 1, wherein the flexible backing is polyester.

7. The skin patch according to claim 3, wherein the tackifier is rosin ester derivative and the plasticizer is liquid paraffin.

8. The skin patch according to claim 3, wherein the flexible backing is polyester.

\* \* \* \* \*